(12) United States Patent
Taimisto

(10) Patent No.: US 6,792,303 B2
(45) Date of Patent: Sep. 14, 2004

(54) APPARATUS FOR IMPROVED SENSOR ACCURACY

(75) Inventor: Miriam H. Taimisto, San Jose, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 529 days.

(21) Appl. No.: 09/854,329

(22) Filed: May 11, 2001

(65) Prior Publication Data

US 2002/0167313 A1 Nov. 14, 2002

(51) Int. Cl.[7] .................................................. A61B 5/05
(52) U.S. Cl. ...................................................... 600/424
(58) Field of Search .......................... 600/424, 407–409, 600/473, 474, 475, 430–432; 128/899

(56) References Cited

U.S. PATENT DOCUMENTS

| | | | |
|---|---|---|---|
| 5,480,687 A | * 1/1996 | Heming et al. | 427/573 |
| 5,622,169 A | * 4/1997 | Golden et al. | 600/424 |
| 5,729,129 A | 3/1998 | Acker | |
| 5,819,749 A | * 10/1998 | Lee et al. | 128/899 |
| 6,070,337 A | * 6/2000 | Wallrafen | 33/708 |
| 6,073,043 A | 6/2000 | Schneider | |
| 6,161,032 A | * 12/2000 | Acker | 600/424 |
| 6,313,401 B1 | * 11/2001 | Triller et al. | 174/52.2 |
| 6,464,693 B1 | * 10/2002 | Andrews et al. | 606/15 |

FOREIGN PATENT DOCUMENTS

WO   WO 00/10456   3/2000

* cited by examiner

Primary Examiner—Francis J. Jaworski
Assistant Examiner—Ruby Jain
(74) Attorney, Agent, or Firm—Bingham McCutchen LLP

(57) ABSTRACT

An electromagnetic sensor capable of maintaining its accuracy through temperature cycling is provided. The sensor element material of an electromagnetic sensor is covered by an encapsulant having substantially similar thermal expansion values as the sensor element material. By matching the thermal expansion values of the components, changes in component orientation may be minimized during temperature cycling thus reducing the need for recalibration of the sensor assembly. In one embodiment the encapsulant is doped with a ceramic material or glass microspheres to achieve a thermal expansion coefficient similar to the thermal expansion coefficient of the copper sensor element material.

37 Claims, 1 Drawing Sheet

APPARATUS FOR IMPROVED SENSOR ACCURACY

TECHNICAL FIELD

The present invention relates generally to sensors and, more particularly, to electromagnetic sensors used to provide location data in medical procedures.

BACKGROUND OF THE INVENTION

Electromagnetic sensors may sometimes be used in medical procedures. For example, electromagnetic sensors may be incorporated into catheters or other invasive medical devices used, e.g., for electrophysiological applications, to provide very accurate location data. An example of a system that employs an arrangement of orthogonally positioned sensors for providing three-dimendional position coordinates of the location of the sensors is shown and described in PCT publication WO 00/10456, entitled "Intrabody Navigation System for Medical Applications," which is hereby expressly and fully incorporated herein by reference.

In particular, an orthogonal arrangement of at least three sensors, which are typically composed of a metallic core, such as copper coil, is mounted in close proximity to each other on a locatable device, such as at the distal end of a catheter, and is used to receive (or transmit) electromagnetic wave energy in a classic x-y-z Cartesian coordinate system. In this manner, the moving object can be located with respect to a fixed frame of reference, thereby allowing an attending physician to locate the moving object within the body of a patient. During assembly of the sensor arrangement, the respective locations of the orthogonal sensor devices are placed in an optimum orientation, and are then fixed, typically by encapsulating the entire sensor arrangement in a potting or adhesive material, such as an ultraviolet (UV) adhesive, resulting in a self-contained and easily packagable and transportable sensor device.

Despite this encapsulation process, these sensor devices may experience a loss of accuracy as a result of changes in environmental conditions. Specifically, it has been noted that various temperature cycling (e.g., when the sensor is exposed to extremely high and/or low temperature during shipping, storage, use, and assembly) appears to reduce the accuracy of the sensors. Thus, the sensors often need to be recalibrated when the sensors are exposed to temperature cycling, and often must be discarded if found to be inaccurate. In the worst case, the object to which the sensors are mounted must also be discarded if the sensor assembly experiences a loss of accuracy after it is installed on the object. Therefore, it would be highly desirable to have an electromagnetic sensor that is able to retain its accuracy during temperature cycling.

SUMMARY OF THE INVENTION

The present inventions are directed to sensor assemblies that are capable of retaining their accuracy during temperature cycling.

In accordance with a first aspect of the present inventions, a sensor assembly comprises a number of sensor elements that are covered by an encapsulant exhibiting a coefficient of thermal expansion approximately equal to that of the sensor elements. In this manner, the sensor elements and encapsulant expand and contract at substantially the same rates when exposed to environmental fluctuations, thereby minimizing displacement of the sensor elements. In order to ensure approximate equality between the first and second coefficients of thermal expansion, the curable adhesive can be conveniently doped with an additive. For example, if the coefficient of thermal expansion of the curable adhesive is greater than the coefficient of thermal expansion of the sensor elements, an additive exhibiting a coefficient of thermal expansion less than that of the sensor elements can be used. By way of non-limiting example, ceramic, e.g., aluminum oxide, magnesium oxide, or silicon oxide, can be used for this purpose. Alternatively, the adhesive may inherently exhibit a coefficient of thermal expansion that is approximately equal to the coefficient of thermal expansion of the sensor elements, thereby obviating the need to dope the adhesive.

In accordance with a second aspect of the present inventions, a sensor assembly comprises a number of sensor elements. The number of sensor elements is covered by an encapsulant comprising a curable adhesive and an additive. The additive exhibits a coefficient of thermal expansion less than that of the sensor elements. For example, ceramic material, such as aluminum oxide, magnesium oxide, or silicon oxide, can be used. Thus, if the coefficient of thermal expansion of the curable adhesive is greater than that of the sensor elements, the coefficient of thermal expansion of the encapsulant can be lowered to more closely match that of the sensor elements.

In accordance with a third aspect of the present inventions, a medical sensor assembly comprises a number of sensor elements that are configured to provide location data during medical procedures. The number of sensor elements is covered by an encapsulant comprising a curable adhesive and an additive. The additive is used to modify the coefficient of thermal expansion of the encapsulant to a suitable value. The coefficient of thermal expansion of the additive can be less than that of the sensor elements. In this case, ceramic material, such as aluminum oxide, magnesium oxide, or silicon oxide, can be used as the additive. The coefficient of thermal expansion of the additive can alternatively be between that of the adhesive and sensor elements. In this case, glass microspheres can be used as the additive. Thus, in either case, if the coefficient of thermal expansion of the curable adhesive is greater than that of the sensor elements, the coefficient of thermal expansion of the encapsulant can be lowered to more closely match that of the sensor elements.

In accordance with a fourth aspect of the present inventions, a method of making a sensor assembly comprises selecting a number of sensor elements and selecting an encapsulant having a coefficient of thermal expansion that is based on that of the sensor elements. By way of non-limiting example, the coefficients of thermal expansion of the sensor elements and encapsulant can be approximately equal. The coefficient of thermal expansion of the encapsulant can be modified to a suitable level by doping an adhesive with an additive. The coefficient of thermal expansion of the additive can be less than that of the sensor elements. In this case, ceramic material, such as aluminum oxide, magnesium oxide, or silicon oxide, can be used as the additive. The coefficient of thermal expansion of the additive can alternatively be between that of the adhesive and sensor elements. In this case, glass microspheres can be used as the additive. Thus, in either case, if the coefficient of thermal expansion of the curable adhesive is greater than that of the sensor elements, the coefficient of thermal expansion of the encapsulant can be lowered to more closely match that of the sensor elements. The encapsulant is then ultimately used to cover the number of sensor elements.

In accordance with the aforementioned aspects of the invention, the sensor elements can comprise a metallic material, such as copper coils. The number of sensor elements can be one or more. If the number is greater than one, the encapsulant can cover the sensor elements to form an integral assembly. In medical applications, the sensor assembly is preferably configured for installation on a catheter or other device that can be introduced into the vasculature of a patient, and operated to provide location data during medical procedures.

DESCRIPTION OF THE PREFERRED EMBODIMENTS

Figure 1:
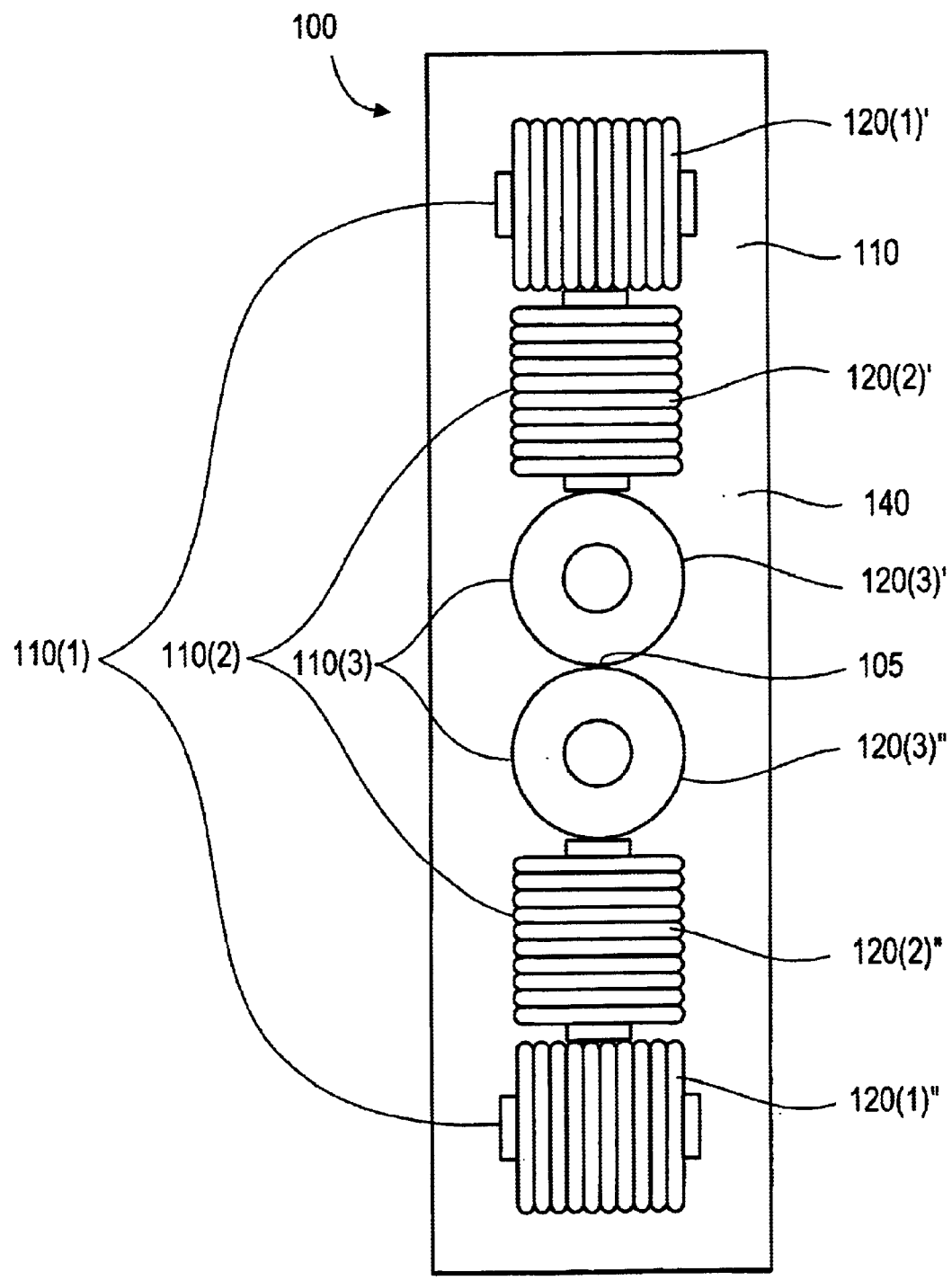
FIG. 1 illustrates an electromagnetic sensor with a copper coil core covered by an adhesive encapsulant.

It has been discovered that the large temperature variations to which the electromagnetic sensors may be exposed, for example, outside the range of 0–105° C., causes the sensor components, such as the metallic core and the encapsulant, to expand and contract at different rates due to the varied coefficients of thermal expansion (CTE) exhibited by the different sensor components. As these components expand and contract at different rates, they will often move or re-orient themselves relative to other components. The changes in the orientation of the sensor components that result from temperature variations may cause the sensors to lose their calibration accuracy.

Referring first to FIG. 1, the present invention provides for a sensor assembly 100 that can be exposed to significant temperature changes without losing calibration accuracy. The sensor assembly 100 includes three sensors 110(1), 110(2), and 110(3) that act as independent magnetic field components. The sensors 110 are arranged in a specific orientation and can be mounted to any movable device to provide accurate positional data as the device is moved through a patient's body.

Specifically, sensors 110(1), 110(2), and 110(3) respectively include three pairs of sensor elements 120(1)' and 120(1)", 120(2)' and 120(2)", and 120(3)' and 120(3)". In the illustrated embodiment, each pair of sensor elements is located on opposite sides of, and equidistant from, reference point 105. Thus, all of the sensor element pairs 120(1), 120(2), and 120(3) share the same reference point, so that the measured magnetic field components are representative of the field component values at the single reference point 105, instead of at three different points. Because of the symmetric disposition of the sensor elements 120 with respect to the reference point 105, the measured magnetic field components are representative of the field components at the reference point, despite the individual sensor elements 120 not being centered on the reference point 105. Further details regarding the design and use of this sensor arrangement for purposes of locating devices within a patient are disclosed in PCT publication WO 00/10456, which has previously been incorporated herein by reference.

The sensors 110 are covered by an encapsulant 140, which preferably is non-conductive, non-magnetic, and capable of being applied to and hardened into a firm shape around and in contact with the sensor elements 120. For example, base and doped curable adhesives, ceramics, rubber compounds, injection-molded thermoplastics, and thermoset plastics can be used. To ensure that the calibration accuracy of the sensors 110 is maintained even when exposed to changing environmental conditions, the composition of the sensors 110 and encapsulant 140 exhibit substantially the same or similar CTE values, so that the sensors 110 and encapsulant 140 expand and contract at substantially the same rate when exposed to any given environmental condition. In this manner, there is little or no change in sensor orientation, and thus little or no loss in calibration accuracy.

In the illustrated embodiment, each of the sensor elements 120 comprises a copper coil, and the encapsulant 140 comprises a commercially available adhesive, such as Dymax® UV Adhesive (series 9001). The CTE values of the copper coils and the Dymax® UV Adhesive (as commercially available) are $16.6 \times 10^{-6}/°$ C. and $100 \times 10^{-6}/°$ C., respectively. To more closely match the CTE values of the sensor elements 120 and encapsulant 140, the CTE value of the encapsulant 140 is modified by doping the Dymax® UV adhesive with additives, which preferably have CTE values that are less than that of copper so that CTE equivalence between the sensor elements 120 and encapsulant 140 can ultimately be achieved. In this case, ceramic-based powders, such as Aluminum Oxide, Magnesium Oxide, and Silicon Oxide, which exhibit respective CTE values of $7.5 \times 10^{-6}/°$ C., $12.8 \times 10^{-6}/°$ C., and $2.0 \times 10^{-6}/°$ C., may be used as the additive. The encapsulant 140 should be able withstand temperature cycling without stress cracking that may otherwise be caused by the sensor elements. Thus, care must be taken in choosing the appropriate type and amount of additive for doping the UV adhesive.

The concentration of additive to be mixed into the adhesive in order to equate the CTE values of the sensor elements 120 and encapsulant 140 can be found by the following equations:

$$x = \frac{(CTE_{sensor} - CTE_{additive})}{(CTE_{adhesive} - CTE_{additive})},$$
$$y = 100(1-x),$$

where x and y are the respective concentrations of the adhesive and additive in the encapsulant 120 by weight or volume, $CTE_{sensor}$ is the CTE value of the sensor element 120, $CTE_{adhesive}$ is the CTE value of the adhesive, and $CTE_{additive}$ is the CTE value of the additive. Thus, to equate the CTE values of the copper sensor elements 120 and encapsulant 140, the concentration of Aluminum Oxide, Magnesium Oxide, and Silicon Oxide to be added to the Dymax® UV adhesive will be 90.2%, 95.6%, and 85.1%, respectively.

One skilled in the art would understand that the present inventions do not restrict the composition of the additive to those listed herein, but rather allows for any material that would modify the thermal properties of the encapsulant 140, such that its CTE is more closely matched to that of the sensor elements 120. Thus, although the CTE values of the sensor elements 120 and encapsulant 140 preferably match, the use of an additive that has a CTE value greater than the CTE value of the sensor elements 120, but less than the CTE value of the adhesive, would still be advantageous to more closely (although not substantially) match the CTE values of the sensor elements 120 and encapsulant 140. For instance, the adhesive can be doped with glass microspheres, such as Litespheres™ (obtained from MO-SCI Corporation, located in Rolla, Mo.) to substantially lower the CTE value of the encapsulant 140. At a 95% concentration level, the resulting CTE value of the encapsulant 140 will near that of the Litespheres™ ($55 \times 10^{-6}/°$ C.), reducing the resulting CTE value of the encapsulant 140 to almost half of the pre-doped CTE value of the encapsulant 140. It should also be noted that the encapsulant 140 can be formed of an adhesive inherently having a CTE value that is similar to the CTE value of the sensor elements 120, thereby obviating the need to mix additives into the adhesive to match its CTE value to that of the sensor elements 120.

Although particular embodiments of the present invention have been shown and described, it will be understood that it is not intended to limit the invention to the preferred embodiments and it will be obvious to those skilled in the art that various changes and modifications may be made without departing from the spirit and scope of the present invention. Thus, the invention is intended to cover alternatives, modifications, and equivalents, which may be included within the spirit and scope of the invention as defined by the claims. All publications, patents, and patent applications cited herein are hereby incorporated by reference in their entirety for all purposes.

What is claimed is:

1. A sensor assembly, comprising:
   a number of sensor elements exhibiting a first coefficient of thermal expansion; and
   an encapsulant covering said number of sensor elements, said encapsulant comprising a curable adhesive doped with an additive, such that said encapsulate exhibits a second coefficient of thermal expansion approximately equal to said first coefficient of thermal expansion.

2. The sensor assembly of claim 1, wherein said additive exhibits a third coefficient of thermal expansion lower than said first coefficient of thermal expansion.

3. The sensor assembly of claim 1, wherein said additive comprises a ceramic material.

4. The sensor assembly of claim 1, wherein said additive comprises a material selected from the group consisting of Aluminum Oxide, Magnesium Oxide, and Silicon Oxide.

5. The sensor assembly of claim 1, wherein said number of sensor elements comprises metallic material.

6. The sensor assembly of claim 1, wherein said number of sensor elements comprises a respective number of copper coils.

7. The sensor assembly of claim 1, wherein said number of sensor elements comprises a plurality of sensor elements.

8. The sensor assembly of claim 1, wherein said number of sensor elements comprises a plurality of sensor elements, and said encapsulant covers said plurality of sensor elements to form an integral sensor assembly.

9. The sensor assembly of claim 1, wherein said number of sensor elements is configured to provide location data for medical procedures.

10. The sensor assembly of claim 1, wherein said sensor assembly is configured for installation on catheter.

11. A sensor assembly, comprising:
    a number of sensor elements exhibiting a first coefficient of thermal expansion; and
    an encapsulant covering said number of sensor elements, said encapsulant comprising a curable adhesive and an additive, wherein said curable adhesive exhibits a second coefficient of thermal expansion greater than said first coefficient of thermal expansion, and said additive exhibits a third coefficient of thermal expansion less than said first coefficient of thermal expansion.

12. The sensor assembly of claim 11, wherein said additive comprises a ceramic material.

13. The sensor assembly of claim 11, wherein said additive comprises a material selected from the group consisting of Aluminum Oxide, Magnesium Oxide, and Silicon Oxide.

14. The sensor assembly of claim 11, wherein said number of sensor elements comprises metallic material.

15. The sensor assembly of claim 11, wherein said number of sensor elements comprises a respective number of copper coils.

16. The sensor assembly of claim 11, wherein said number of sensor elements comprises a plurality of sensor elements.

17. The sensor assembly of claim 11, wherein said number of sensor elements comprises a plurality of sensor elements, and said encapsulant covers said plurality of sensor elements to form an integral sensor assembly.

18. The sensor assembly of claim 11, wherein said number of sensor elements is configured to provide location data for medical procedures.

19. The sensor assembly of claim 11, wherein said sensor assembly is configured for installation on catheter.

20. A medical sensor assembly, comprising:
    a number of sensor elements configured to provide location data for medical procedures, wherein said number of sensor elements exhibits a first coefficient of thermal expansion; and
    an encapsulant covering said number of sensor elements, said encapsulant comprising a curable adhesive and an additive, wherein said curable adhesive exhibits a second coefficient of thermal expansion greater than said first coefficient of thermal expansion, and said additive exhibits a third coefficient of thermal expansion less than said first coefficient of thermal expansion.

21. The medical sensor assembly of claim 20, wherein said additive comprises a ceramic material.

22. The medical sensor assembly of claim 20, wherein said additive comprises a material selected from the group consisting of Aluminum Oxide, Magnesium Oxide, and Silicon Oxide.

23. The medical sensor assembly of claim 20, wherein said additive comprises microspheres.

24. The medical sensor assembly of claim 20, wherein said number of sensor elements comprises metallic material.

25. The medical sensor assembly of claim 20, wherein said number of sensor elements comprises a respective number of copper coils.

26. The medical sensor assembly of claim 20, wherein said number of sensor elements comprises a plurality of sensor elements.

27. The medical sensor assembly of claim 20, wherein said number of sensor elements comprises a plurality of sensor elements, and said encapsulant covers said plurality of sensor elements to form an integral sensor assembly.

28. The medical sensor assembly of claim 20, wherein said sensor assembly is configured for installation on a catheter.

29. A medical sensor assembly, comprising:
    a number of sensor elements configured to provide location data for medical procedures, wherein said number of sensor elements exhibits a first coefficient of thermal expansion; and
    an encapsulant covering said number of sensor elements, said encapsulant comprising a curable adhesive and an additive, wherein said curable adhesive exhibits a second coefficient of thermal expansion greater than said first coefficient of thermal expansion, and said additive exhibits a third coefficient of thermal expansion between said first and second coefficients of thermal expansion.

30. The medical sensor assembly of claim 29, wherein said additive comprises a ceramic material.

31. The medical sensor assembly of claim 29, wherein said additive comprises a material selected from the group consisting of Aluminum Oxide, Magnesium Oxide, and Silicon Oxide.

32. The medical sensor assembly of claim 29, wherein said additive comprises microspheres.

33. The medical sensor assembly of claim 29, wherein said number of sensor elements comprises metallic material.

34. The medical sensor assembly of claim 29, wherein said number of sensor elements comprises a respective number of copper coils.

35. The medical sensor assembly of claim 29, wherein said number of sensor elements comprises a plurality of sensor elements.

36. The medical sensor assembly of claim 29, wherein said number of sensor elements comprises a plurality of sensor elements, and said encapsulant covers said plurality of sensor elements to form an integral sensor assembly.

37. The medical sensor assembly of claim 29, wherein said sensor assembly is configured for installation on a catheter.

* * * * *